United States Patent [19]
Doyle et al.

[11] Patent Number: 6,071,706
[45] Date of Patent: Jun. 6, 2000

[54] STABILISING MEDIUM FOR ALPHAGST IN URINE FOR USE IN AN ENZYME IMMUNOASSAY

[75] Inventors: John Martin Doyle; Cormac Gerard Kilty, both of County Dublin, Ireland

[73] Assignee: Biotrin Intellectual Properties Limited, County Dublin, Ireland

[21] Appl. No.: 08/817,696

[22] PCT Filed: Oct. 17, 1994

[86] PCT No.: PCT/IE94/00050

§ 371 Date: Apr. 17, 1997

§ 102(e) Date: Apr. 17, 1997

[87] PCT Pub. No.: WO96/12191

PCT Pub. Date: Apr. 25, 1996

[51] Int. Cl.[7] .................. G01N 33/53; G01N 33/573; C12Q 1/48; C12N 9/10

[52] U.S. Cl. .............. 435/7.1; 435/7.1; 435/7.4; 435/15; 435/193; 435/252.3; 435/252.33; 435/320.1; 435/325; 536/23.5; 536/23.2; 536/23.1

[58] Field of Search .................. 435/7.4, 15, 7.1, 435/193, 252.3, 252.33, 320.1, 325; 536/23.5, 23.2, 23.1

[56] References Cited

U.S. PATENT DOCUMENTS 4,273,756  6/1981  Ling et al. .
5,217,868  6/1993  Kilty et al. .
5,264,419  11/1993  Horwell et al. .
5,278,316  1/1994  Horwell et al. .
5,817,497  10/1998  Goli et al. .
5,874,248  2/1999  Hillman et al. .

FOREIGN PATENT DOCUMENTS 692761       1/1996   European Pat. Off. .
4-025763     1/1992   Japan .
WO 93/22452  11/1993  WIPO .

OTHER PUBLICATIONS

Backman et al, Kidney International, 33:571–577, 1988.

Primary Examiner—Nita Minnifield
Assistant Examiner—Padma Baskar
Attorney, Agent, or Firm—Birch, Stewart, Kolasch & Birch, LLP

[57] ABSTRACT

Stabilizing medium for urinary αGST contains a stabilizing amount of a non-enzyne protein, such as a mixture of equal amounts (w/v) of bovine serum albumin and gelatin hydrolysate, chelating agent and a buffer, such that the medium has a pH in the range 7.0–7.5, the medium being effective to prevent loss of αGST immunological activity. The stabilizing medium can be used to store urine samples at temperatures of the order of −20° C. without any loss of αGST immunoreactivity of the type observed in samples which are stored without such a stabilizing medium. The stabilizing medium also improves the immunoreactivity of αGST when added to fresh urine which is stored temporarily at 2–8° C. prior to assay for up to two hours.

30 Claims, No Drawings

STABILISING MEDIUM FOR ALPHAGST IN URINE FOR USE IN AN ENZYME IMMUNOASSAY

TECHNICAL FIELD

This invention relates to a stabilising medium for alpha glutathione S transferase (αGST) in urine and the use thereof in an enzyme immunoassay for αGST.

BACKGROUND ART

Glutathione transferases (GSTs) are enzymes which are found in highly varying amounts in human tissues. The enzymes form three major classes, designated α, π and μ. These three classes of enzyme are quite distinct in their properties.

αGST is found in the proximal tubule region of the kidney and is released into the urine in normal individuals, as confirmed by enzyme immunoassay and western blot analysis (Campbell, J. A. H. et al (1991) Cancer (Philadelphia), 67, 1608–1613). Any event which precipitates proximal tubule damage may cause the release of αGST into urine leading to an increase in normal urinary levels. Thus, an elevation of urinary αGST levels may be indicative of proximal tubule damage (Sherman, R. A. et al. (1985) Urermia Investigation, 8, 111–115). Recent work has shown that cisplatin induced proximal tubule damage in Wistar rats is associated with elevated levels of urinary αGST activity and decreased serum creatinine clearance (Stojanov, M. et al. (1994) Clin. Chem., 14, 1125), and that acute tubular necrosis and renal transplant infarction in humans result in a rapid increase of both α and π GST levels (Sundberg, A. G. M. et al. (1994) Nephron 67, 308–316).

The ability to use urine as a sample of a body fluid for the detection and determination of an enzyme indicative of kidney damage and, in particular, a particular region of the kidney is an advantage, especially because no invasive collection of the body sample is required. In general, one wishes to estimate αGST in patients who are seriously ill and minimisation of any unnecessary trauma is very desirable.

Traditionally, radioimmunoassay has been used for estimating αGST in urine with the attendant disadvantages of using a radio-labelled substance.

Frequently, it is not possible to carry out the necessary estimation of urinary αGST for some considerable time, such as days, after a sample has been collected. Accordingly, it is often necessary to store the urine sample at very low temperatures, typically of the order of –20° C. However, it is found that on storing urinary αGST at such low temperatures leads to a loss of immunoreactivity and thus a poor sensitivity of any immunoassay. This loss of immunoreactivity is most likely due to freeze-thaw denaturation.

Accordingly, there is a need for a medium which enables one to store αGST in urine at temperatures of the order of –20° C. without any substantial loss of immunoreactivity of αGST in an immunoassay used to detect the αGST, when required.

DISCLOSURE OF INVENTION

Accordingly, the invention provides a stabilising medium for αGST in urine, which comprises a stabilising amount of a non-enzyme protein, a chelating agent and a buffer, such that the medium has a pH in the range 7.0–7.5, and the medium being effective to prevent loss of αGST immunological activity.

The stabilising medium according to the invention can be used to store urine samples at temperatures of the order of –20° C. without any loss of immunoreactivity. However, additionally, the stabilising medium according to the invention is found to improve immunoreactivity when added to fresh urine which is stored temporarily at 2–8° C. prior to assay for up to two hours.

Preferably, the non-enzyme (αGST) protein is an albumin.

The protein can be a mixture of albumin and hydrolysed gelatin. Such gelatin hydrolysates are commercially available for example from Sigma Chemicals (Code G-0262 enzymatically generated).

An especially preferred albumin (non-hydrolysed) is a serum albumin, especially bovine serum albumin (BSA).

A preferred mixture of a serum albumin and a hydrolysed gelatin is a mixture of equal amounts (w/v) of bovine serum albumin and gelatin hydrolysate.

The concentration of non-enzyme protein is suitably in the range 5–15% w/v, more particularly of the order of 10% w/v.

The chelating agent is suitably an alkali metal salt of EDTA.

The stabilising medium suitably has a salt concentration in the range 4–5% w/v. Especially suitable salts or alkali metal salts, more especially sodium chloride.

The inclusion of a salt such as sodium chloride aids in the dissolution of albumin and/or gelatin hydrolysate or other non-enzyme proteins used and which has the requisite stabilising properties.

Although not wishing to be bound by any theoretical explanation of the invention, it is considered that the salt may function by reducing assays 'backgrounds', i.e. non-specific binding.

The stabilising medium also suitably contains a protease inhibitor. A preferred protease inhibitor is a trypsin inhibitor such as aprotinin.

The buffer is suitably a zwitterionic buffer of the type described by N. E. Good. and S. Izawa ((1972) Methods in Enzymol., 24, Part B, 53). An especially suitable buffer is HEPES at a pH of 7.3.

The stabilising medium according to the invention can also include other additives, for example, various antimicrobial agents or preservatives.

Suitable preservatives include sodium azide and preservatives containing mercurothiolate also known as thiomersal or thiomerosal.

The stabilising medium according to the invention will be mixed prior to storing with a urine sample which is to be assayed for αGST following storing at –20° C. at a given period of time.

The invention also provides a method for the quantitative determination of αGST in urine, which comprises contacting a urine sample with an insolubilised form of anti-αGST IgG, the urine sample having been pre-treated with a stabilising medium as hereinbefore defined, determining the amount of αGST bound to the anti-αGST IgG by contacting the bound αGST with enzyme-labelled anti-αGST IgG and measuring the activity of the enzyme label.

The stabilising medium according to the invention enables one to achieve a sensitivity in an immunoassay for urinary αGST which correlates closely with that obtained when an immunoassay is carried out on what are referred to in the art as fresh urine samples. In contrast with the situation when urine samples are stored at −20° C. in the absence of the stabilising medium, there is substantially no loss of immunoreactivity following the storage of such samples in the presence of the stabilising medium according to the invention, as hereinafter demonstrated in the Examples.

The preferred enzyme label is a peroxidase, more especially horseradish peroxidase.

Another preferred peroxidase conjugate is a biotinylated avidin (includes streptavidin)-peroxidase complex, which may be used with an antibody-biotin conjugate to amplify the enzyme assay in conventional manner. In such an enzyme assay antigen insolubilised on solid phase antibody binds to the antibody-biotin conjugate which in turn binds to the biotinylated avidin/streptavidin-peroxidase complex, whereupon the peroxidase activity is measured.

Further, preferably, the anti-αGST IgG-HRP-conjugate used in the enzyme immunoassay is in a liquid stable form in a stabilising medium comprising a stabilising amount of cytochrome c and a stabilising amount of serum albumin, a surfactant, a polyol and a buffer, such that the medium has a pH of the order of 6.5 and that the final concentration of polyol is in the range 5–15% v/v.

The cytochrome c is preferably present in an amount of 0.02–2% weight by volume. Whereas the concentration of cytochrome c can be increased to above 2% weight by volume without substantially affecting stabilisation, decreasing the concentration below about 0.02% weight by volume results in a decrease in the stabilising effect of the buffer.

By cytochrome c herein is meant a cytochrome in which there are covalent linkages between the side chains of the heme moiety and the protein.

The stabilising protein is preferably a serum albumin which is present in an amount of 0.5–2% weight by volume.

An especially suitable serum albumin is bovine serum albumin (BSA). Whereas the quantity of BSA can be increased to above 2% weight by volume without substantially affecting stabilisation as in the case of the cytochrome c component, if the concentration is decreased below about 0.5% weight by volume the stabilising effect of the buffer is decreased.

The serum albumin can be supplemented by further stabilising protein, for example, foetal calf serum which is rich in BSA.

The surfactant is preferably a non-ionic surfactant selected from polyoxyethylene esters of fatty acids, polyoxyethylene sorbitan esters, polyoxyethylene alcohols, polyoxyethylene isoalcohols, polyoxyethylene ethers, polyoxyethylene esters, polyoxyethylene-p-t-octylphenols or octylphenyl-ethylene oxide condensates, ethylene oxide condensates with fatty alcohols, polyoxyethylene nonylphenols, and mixtures of polyalkylene glycols or a mixture thereof.

Especially preferred non-ionic surfactants include: polyethylene sorbitan esters sold under the Trade Mark Tween, especially polyoxyethylene sorbitan monolaurate or Tween 20, but also Tween 60 and Tween 80; polyoxyethylene ethers sold under the Trade Mark Triton, such as Triton X100, Triton X114, Triton X100E and Triton N101, and Brij; an octylphenyl-ethylene oxide condensate sold under the Trade Mark Nonidet P40; ethylene oxide condensates of fatty alcohols sold under the Trade Mark Lubrol, especially Lubrol PX; and a mixture of one part by weight of polyethylene glycol and four parts by weight of polypropylene glycol sold under the Trade Mark Synperonic F108. (Tween, Triton, Brij, Nonidet, Lubrol and Synperonic are all Trade Marks).

An especially suitable surfactant is a Synperonic F108.

The polyol stabilises protein-protein interactions. Suitable polyols include glucose, glycerol, mannitol, sorbitol and sucrose or a mixture thereof. An especially preferred polyol is glycerol at a final concentration of the order of 10% v/v.

An especially suitable buffer is phosphate buffered saline.

A stabilising medium for the anti-αGST IgG-HRP-conjugate can also include other additives depending on the nature of the enzyme conjugate, for example, various antimicrobial agents, preservatives and protease inhibitors, agents which stabilise protein—protein interactions, antioxidants and colouring agents which aid in identification.

A suitable antimicrobial agent is gentamicin.

Suitable preservatives include preservatives containing mercurothiolate also known as thiomersal or thiomerosal.

A suitable protease inhibitor is, for example, a trypsin inhibitor such as aprotinin.

A suitable colouring agent is carmine dye.

The invention will be further illustrated by the following Examples.

BEST MODE FOR CARRYING OUT THE INVENTION

EXAMPLE 1

A stabilising medium for urinary αGST with a pH of 7.3 was prepared from the following reagents:

| Reagents | |
| --- | --- |
| HEPES | 0.5 M |
| Na$_2$EDTA | 10 mM |
| NaCl | 4.5% (w/v) |
| BSA | 5% (w/v) |
| Gelatin hydrolysate | 5% (w/v) |
| Aprotinin | 10 µg/ml |
| Thiomersal | 0.01% (w/v) |
| Sodium azide | 0.05% (w/v) |

All of the above components were added to 80% of the final volume of deionised water and the pH adjusted to 7.3 with NaOH. The solution was then brought to the final volume with deionised water. In the case of the addition of the BSA and the gelatin hydrolysate, it is important that these are added separately and care should be taken to ensure that the first component is completely dissolved before the second component is added.

The stabilising medium so prepared is used for stabilising urinary αGST by adding one part of the medium to four parts of urine (⅕ dilution), mixing gently and freezing the sample at −20° C. or storing temporarily at 2–8° C. prior to assay for up to two hours.

EXAMPLE 2

A stabilising medium for anti-αGST IgG-HRP-conjugate with a pH of 6.5 was prepared from the following reagents:

| Reagent | Quantity |
| --- | --- |
| NaCl | 8.000 g |
| NaH$_2$PO$_4$.2H$_2$O | 0.260 g |
| Na$_2$H$_2$PO$_4$.2H$_2$O | 1.425 g |
| Cytochrome c | 0.250 g |
| Synperonic F108 | 10.000 g |
| BSA | 10.000 g |
| Foetal calf serum | 25.000 ml |
| Thiomersal | 0.100 g |
| Gentamicin | 0.100 g |
| Carmine dye | 0.930 g |
| Concentrated HCl (to adjust pH) | variable |
| Deionised water | variable |
| Made up to 1000 ml with deionised water | |

700 ml of deionised water was added to a glass container. To this was added the NaCl, NaH$_2$PO$_4$.2H$_2$O, Na$_2$H$_2$PO$_4$.2H$_2$O and thiomersal with stirring until dissolution of the reagents occurred. The Synperonic F108 was then added to the solution following by stirring until the surfactant dissolved. The pH of the solution was then checked and adjusted to pH 6.5 with 5M HCl. The BSA was then added to the solution and allowed to dissolve. To this was then added the foetal calf serum with further stirring until dissolution occurred. The gentamicin, cytochrome c and carmine dye were then added with further stirring until dissolution occurred. The pH was rechecked and adjusted as necessary to pH 6.5. The final volume was adjusted to 1000 ml and the buffer was filtered through a 0.2 μm filter ready for storage. In use nine parts of the buffer are added to one part glycerol.

EXAMPLE 3

The stability of the anti-αGST IgG-HRP conjugate currently provided in lyophilised form in an enzyme immunoassay kit marketed by Biotrin International Limited under the trade mark Nephkit was investigated in the stabilising medium prepared in Example 2. The Nephkit assay provides a method for the quantitative determination of αGST in urine and can be indicative of proximal tubule damage in the kidney.

100% stability of a 10× concentrate was obtained when the conjugate was stored for twenty four hours at room temperature in the stabilising medium prepared in Example 2.

EXAMPLE 4

Utility of the stabilising medium of Example 1 for stabilising urinary αGST during storage at −20° C.

Nine urine samples (male and female) were obtained and assayed immediately for αGST using the enzyme immunoassay kit marketed by Biotrin International Limited, Mount Merrion, County Dublin, Ireland, under the trade mark Nephkit. The results are shown in column 2 in Table 1.

The samples were then split and the stabilising medium prepared in Example 1 added to one lot (−20° C. (SM)) and not to the other (−20° C.).

The samples were retained at −20° C. for three days after which they were assayed using the Nephkit assay.

It was found that the values obtained for the samples stored at −20° C. in the stabilising medium correlated closely with the original 4° C. (fresh) data. However, examples frozen without the stabilising medium all exhibited a diminution in αGST immunoreactivity. As indicated above this loss of immunoreactivity is most likely due to freeze thawed induced denaturation.

TABLE 1

| | Storage Temperature | | |
| --- | --- | --- | --- |
| Sample | 4° C. | −20° C. [αGST] ng/ml | −20° C. (SM) |
| 1 | 2.62 | 0.58 | 3.01 |
| 2 | 2.63 | 0.81 | 2.93 |
| 3 | 0.44 | 0.00 | 0.71 |
| 4 | 8.54 | 3.64 | 8.43 |
| 5 | 1.40 | 0.43 | 2.15 |
| 6 | 3.30 | 0.95 | 4.43 |
| 7 | 4.12 | 0.93 | 4.29 |
| 8 | 1.80 | 0.43 | 2.13 |
| 9 | 4.31 | 0.50 | 4.88 |

EXAMPLE 5

Stabilisation of Urinary αGST-Spiked Samples

Two urine samples, A and B, were each spiked to five different levels of αGST (10, 25, 50, 100 and 500 ng/ml) and then stored in the presence of the stabilising medium of Example 1 for two days at 4° C. and −20° C. The results are shown in Tables 2 and 3.

It will be observed from Tables 2 and 3 that the presence of the stabilising medium protects αGST against loss of immunological activity which facilitates the detection in the enzyme immunoassay used.

TABLE 2

| | Storage Temperature | |
| --- | --- | --- |
| Sample | 4° C. [αGST] ng/ml | −20° C. (SM) |
| A: 500 | 191.1 | 507.8 |
| A: 100 | 57.22 | 103.2 |
| A: 50 | 29.48 | 47.11 |
| A: 25 | 15.35 | 25.9 |
| A: 10 | 7.71 | 11.82 |

TABLE 3

| | Storage Temperature | |
| --- | --- | --- |
| Sample | 4° C. [αGST] ng/ml | −20° C. (SM) |
| B: 500 | 49.30 | 467.8 |
| B: 100 | 37.30 | 88.95 |
| B: 50 | 17.52 | 45.23 |
| B: 25 | 8.63 | 21.12 |
| B: 10 | 3.40 | 8.26 |

EXAMPLE 6

Two samples, denoted C 200 and D 200, were prepared containing 200 ng/ml αGST and the stabilising medium of Example 1 was added to each sample.

Each of the two samples was then split and the resulting split samples in each case were stored at 4° C. and −20° C.

After storage for two days each of the samples was assayed at different dilutions (1/40–1/320) in assay dilutent using the Nephkit assay procedure referred to in Example 4.

The results are shown in Tables 4 and 5.

It will be apparent from the data set out in Tables 4 and 5 that sample dilution does not affect αGST determination and that storage at −20° C. is surprisingly superior to storage at 4° C.

TABLE 4

| Sample | Storage Temperature | |
|---|---|---|
| | 4° C. [αGST] ng/ml | −20° C. (SM) |
| C200 (1/40) | 106 | 175 |
| (1/80) | 109 | 185 |
| (1/160) | 104 | 188 |
| (1/320) | 111 | 180 |

TABLE 5

| Sample | Storage Temperature | |
|---|---|---|
| | 4° C. [αGST] ng/ml | −20° C. (SM) |
| D200 (1/40) | 141 | 183 |
| (1/80) | 141 | 183 |
| (1/160) | 134 | 180 |
| (1/320) | 128 | 187 |

We claim:

1. A stabilising medium for alpha glutathione S transferase in urine, which comprises a stabilising amount of a mixture of equal amounts (w/v) of bovine serum albumin and gelatin hydrolysate, a chelating agent and a buffer, such that the medium has a pH in the range of 7.0–7.5, and the medium being effective to prevent loss of alpha glutathione S transferase immunological activity.

2. A stabilising medium according to claim 1, wherein the concentration of the bovine serum albumin and gelatin hydrolysate mixture is from about 5% w/v to about 15% w/v.

3. A stabilising medium according to claim 1, wherein the chelating agent is an alkali metal salt of ethylenediaminetetraacetic acid.

4. A stabilising medium according to claim 1, which has a salt concentration in the range 4–5% w/v.

5. A stabilising medium according to claim 4, wherein the salt is an alkali metal salt.

6. A stabilising medium according to claim 4 or 5, wherein the salt is sodium chloride.

7. A stabilising medium according to claim 1, which includes a protease inhibitor.

8. A stabilising medium according to claim 1, wherein the buffer is a zwitterion buffer.

9. A stabilising medium according to claim 8, wherein the buffer is N-[hydroxyethyl]piperazine-N'-[2-ethane sulfonic acid].

10. A stabilising medium according to claim 1, wherein the buffer has a pH of 7.3.

11. A method for the quantitative determination of alpha glutathione S transferase in urine, which comprises contacting a urine sample with an insolubilised form of anti-alpha glutathione S transferase immunoglobulin G, the urine sample having been pre-treated with a stabilising medium according to claim 1, determining the amount of alpha glutathione S transferase bound to the anti-alpha glutathione S transferase immunoglobulin G by contacting the bound alpha glutathione S transferase with enzyme labelled anti-alpha glutathione S transferase immunoglobulin G and measuring the activity of the enzyme label.

12. A method according to claim 11, wherein the enzyme label is a peroxidase.

13. A method according to claim 11 or 12, wherein the peroxidase is horseradish peroxidase.

14. A method according to claim 13, wherein the anti-alpha glutathione S transferase immunoglobulin G-horseradish peroxidase-conjugate, is in a liquid stable form in a stabilising medium comprising a stabilising amount of cytochrome c and a stabilising amount of serum albumin, a surfactant, a polyol and a buffer, such that the medium has a pH of 6.5 and that the final concentration of polyol is in the range of 5–15% v/v.

15. A method of stabilising alpha glutathione S transferase in a urine sample comprising, mixing a urine sample containing alpha glutathione S transferase with a stabilising medium comprising a stabilising amount of a non-enzyme protein, a chelating agent, and a buffer, wherein the pH of the medium is in the range of 7.0–7.5.

16. The method according to claim 15, wherein the non-enzyme protein of the stabilising medium is an albumin.

17. The method according to claim 15 or 16, wherein the non-enzyme protein of the stabilising medium is a mixture of an albumin and a hydrolyzed gelatin.

18. The method according to claim 17, wherein the mixture is a mixture of a serum albumin and a hydrolyzed gelatin.

19. The method according to claim 17, wherein the mixture is a mixture of equal amounts (w/v) of bovine serum albumin and gelatin hydrolysate.

20. The method according to claim 15, wherein the concentration of non-enzyme protein of the stabilising medium is from about 5% w/v to about 15% w/v.

21. The method according to claim 15, wherein the chelating agent of the stabilising medium is an alkali metal salt of ethylenediaminetetraacetic acid.

22. The method according to claim 15, wherein the stabilising medium has a salt concentration in the range of 4–5% w/v.

23. The method according to claim 22, wherein the salt is an alkali metal salt.

24. The method according to claim 22 or 23, wherein the salt is sodium chloride.

25. The method according to claim 15, wherein said stabilising medium includes a protease inhibitor.

26. The method according to claim 15, wherein the buffer of the stabilising medium is a zwitterion buffer.

27. The method according to claim 26, wherein the buffer of the stabilising medium is N-[hydroxyethyl]piperazine-N'-[2-ethane sulfonic acid].

28. The method according to claim 15 wherein the buffer of the stabilising medium has a pH of 7.3.

29. A method of preventing loss of activity of alpha glutathione S transferase in a urine sample comprising, mixing a urine sample containing alpha glutathione S transferase with a stabilising medium comprising a stabilising amount of a non-enzyme protein, a chelating agent, and a buffer, wherein the pH of the medium is in the range of 7.0–7.5.

30. A method of storing a urine sample containing alpha glutathione S transferase comprising, mixing a urine sample containing alpha glutathione S transferase with a stabilising medium comprising a stabilising amount of a non-enzyme protein, a chelating agent, and a buffer, wherein the pH of the medium is in the range of 7.0–7.5.

* * * * *